United States Patent [19]
Sharkey

[11] Patent Number: 5,843,078
[45] Date of Patent: Dec. 1, 1998

[54] RADIO FREQUENCY DEVICE FOR RESURFACING SKIN AND METHOD

[76] Inventor: Hugh R. Sharkey, 935 Corriente Pointe Dr., Redwood City, Calif. 94065-1287

[21] Appl. No.: 886,580

[22] Filed: Jul. 1, 1997

[51] Int. Cl.[6] ..................................................... A61N 1/44
[52] U.S. Cl. ............................ 606/41; 607/104; 607/115
[58] Field of Search ................................ 606/41, 48, 49, 606/50; 607/100–105, 115, 153

[56] References Cited

U.S. PATENT DOCUMENTS

| | | | |
|---|---|---|---|
| 4,832,048 | 5/1989 | Cohen | 606/41 |
| 5,195,959 | 3/1993 | Smith | 606/41 |
| 5,277,696 | 1/1994 | Hagen | 606/50 |
| 5,348,554 | 9/1994 | Imran et al. | 607/105 |
| 5,401,272 | 3/1995 | Perkins | 606/50 |
| 5,458,596 | 10/1995 | Lax et al. | 607/101 |
| 5,584,972 | 12/1996 | LaFontaine et al. | 607/116 |
| 5,685,877 | 11/1997 | Pagedas et al. | 606/41 |

*Primary Examiner*—William E. Kamm
*Assistant Examiner*—George R. Evanisko
*Attorney, Agent, or Firm*—Flehr Hohbach Test Albritton & Herbert LLP

[57] ABSTRACT

A radio frequency device for use on a human to resurface skin having collagen therein. The device includes a handle member having an end portion adapted for engaging the skin. At least one passageway extends through the handle member to an opening at the end portion. An electrically conductive liquid is supplied through the passageway to the opening. An electrode is carried by the end portion in communication with the passageway. Radio frequency energy supplied to the electrode causes the collagen in the skin to contract and thus tighten the skin.

13 Claims, 2 Drawing Sheets

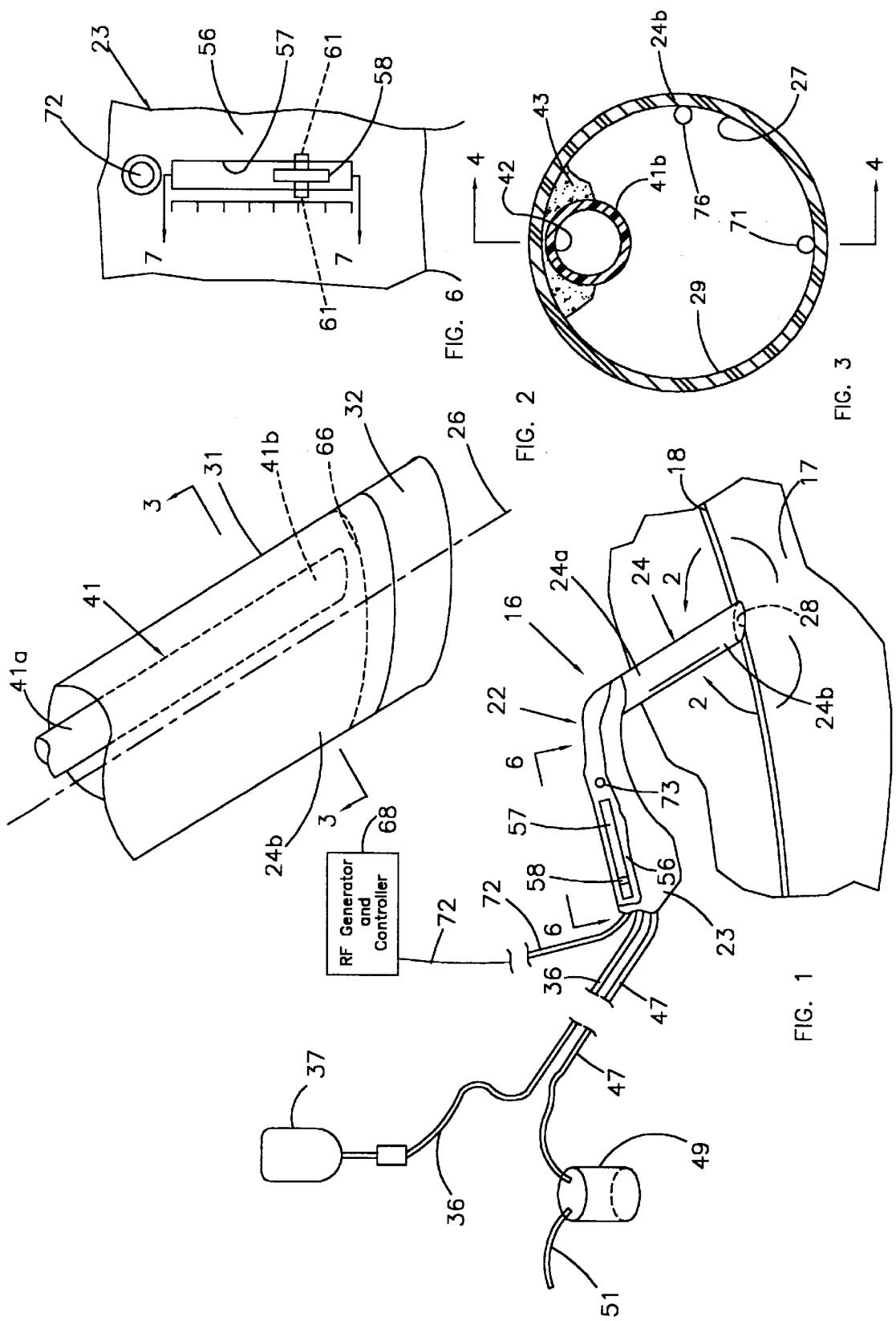

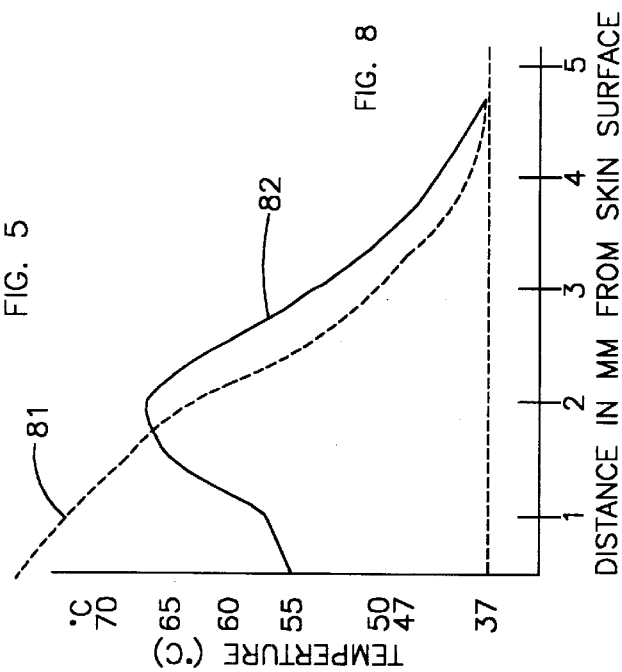
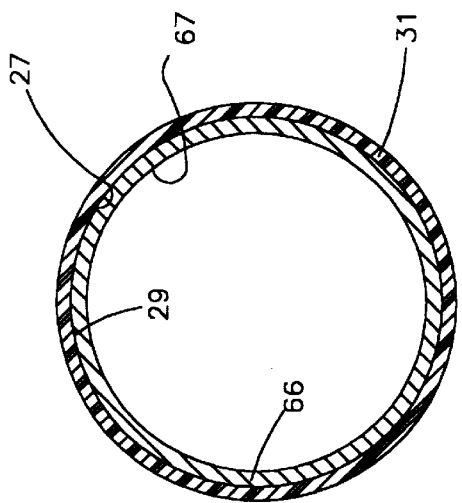
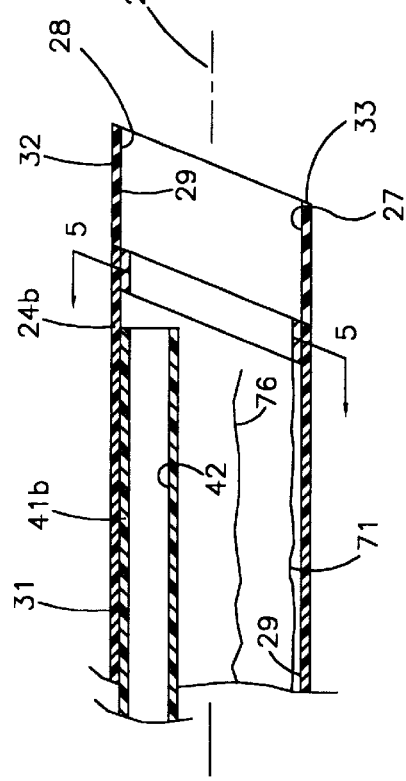
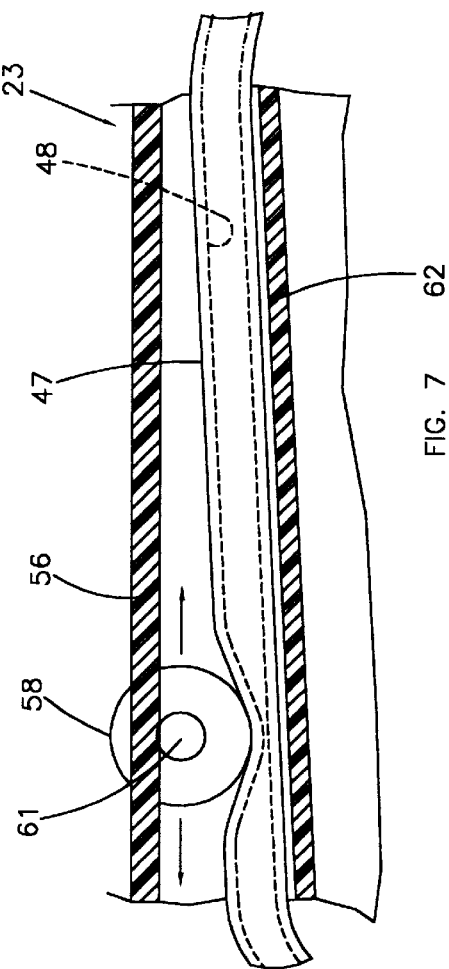

RADIO FREQUENCY DEVICE FOR RESURFACING SKIN AND METHOD

This invention relates to devices and methods for resurfacing skin and, more particularly, to devices and methods for treating wrinkles.

Devices utilizing laser energy exist for resurfacing or tightening skin. These devices burn the skin with a superficial application of laser energy which is sufficient to penetrate the subdermal layers and cause shrinkage of the collagen components of these deep skin layers. Unfortunately, these devices produce a second degree burn in the outer layers of the skin which is painful and results in sloughing of these layers. There is, therefore, a need for a new and improved device which overcomes these advantages.

In general, it is an object of the present invention to provide a radio frequency device and method for resurfacing skin.

Another object of the invention is to provide a radio frequency device and method of the above character in which collagen molecules in the skin are denatured to tighten the epidermis layer of the skin.

Another object of the invention is to provide a radio frequency device and method of the above character in which the subdermal layers of the skin are heated to denature the collagen therein.

Another object of the invention is to provide a radio frequency device and method of the above character which minimizes burning of the superficial layers of the skin.

Another object of the invention is to provide a radio frequency device and method of the above character in which radio frequency energy is carried by an electrically conductive liquid to the surface of the skin.

Another object of the invention is to provide a radio frequency device and method of the above character in which a flow of the electrically conductive liquid engages the skin to actively cool the skin.

Additional objects and features of the invention will appear from the following description in which the preferred embodiments are set forth in detail in conjunction with the accompanying drawings.

FIG. 1 is an isometric view of the radio frequency device for the present invention.

FIG. 2 is an enlarged fragmentary view of a portion of the radio frequency device of FIG. 1 taken along the line 2—2 of FIG. 1.

FIG. 3 is a cross-sectional view of the radio frequency device of FIG. 1 taken along the line 3—3 of FIG. 2.

FIG. 4 is a cross-sectional view of the radio frequency device of FIG. 1 taken along the line 4—4 of FIG. 3.

FIG. 5 is a cross-sectional view of the radio frequency device of FIG. 1 taken along the line 5—5 of FIG. 4.

FIG. 6 is an enlarged fragmentary top plan view of the radio frequency device of FIG. 1 taken along the line 6—6 of FIG. 1.

FIG. 7 is a cross-sectional view of the radio frequency device of FIG. 1 taken along the line 7—7 of FIG. 6.

FIG. 8 is a graph of the optimal temperature gradient across the thickness of the skin achieved with the radio frequency device and method of the present invention.

In general, a radio frequency device is provided for use on a human to resurface skin having collagen therein. The device includes a handle member having an end portion adapted for engaging the skin. At least one passageway extends through the handle member to an opening at the end portion. Means coupled to the handle member supplies an electrically conductive liquid through the passageway to the opening. An electrode is carried by the end portion in communication with the passageway. Means for supplying radio frequency energy to the electrode is included. The radio frequency energy causes the collagen in the skin to contract and thus tighten the skin.

More in particular, a medical apparatus or device 16 is provided for supplying radio frequency energy to the skin 17 of a patient for resurfacing the skin 17 (see FIG. 1). Radio frequency device 16 is particularly suited for treating wrinkles 18 formed in skin 17. The device 16 is made from a body or handle member 22 having handle means in the form of handle 23 adapted for grasping by the operator and an end portion in the form of elongate cylindrical tube 24 adapted for engaging the skin of the patient. Tubular member or tube 24, as shown more specifically in FIGS. 2—5, has proximal and distal extremities 24a and 24b and extends along a central longitudinal axis 26. At least one lumen or passageway 27 extends from proximal extremity 24a to an opening or orifice 28 at distal extremity 24b. First passageway 27 is formed by a cylindrical inner surface 29 of tube 24. Tube 24 has an inner diameter ranging from 0.2 inch to 1.5 inches. The tube 24 has a proximal portion 31 made from any suitable clear material such as polyethylene or polyester and a distal end 32 made from any suitable pliable, non-conductive material such as Buna rubber so as to permit distal end 32 to conform to the shape of the skin 17 on which it is placed. Distal end 32 is secured to proximal portion 31 by any suitable means such as an adhesive (not shown). The distal end 32 has a longitudinal dimension or length of approximately 0.5 inch and is formed with a generally planar end surface 33 disposed at an angle of approximately 45° to 80° relative to longitudinal axis 26.

Handle 23 has a shape adapted for grasping by a human hand, as shown in FIG. 1, and is made from any suitable rigid material such as acrylonitrile butadiene styrene (ABS), nylon, polyethylene or polyester. Tube proximal extremity 24a is connected to handle 23 by any suitable means such as an adhesive (not shown). Alternatively, tube 24 can be formed integral with handle 23 and be within the scope of the present invention.

First passageway 27 has a cross-sectional area to permit a flow of a liquid to travel therethrough to skin 17 at orifice 28. The liquid traveling through the first passageway is an electrically conductive liquid and can be in the form of a liquid having relatively high viscosity, such as two centipoise. Alternatively, the electrically conductive liquid or electrolytic solution can be a saline solution and be within the scope of the present invention. A tubular member or tube 36 extends from a conventional supply pouch or container 37 having the electrolytic solution therein through handle 23 for supplying the electrolytic solution to tube 24. Supply tube 36 can be of any suitable type such as flexible surgical tubing and is provided with an internal passageway (not shown) which communicates with first or supply passageway 27 of tube 24. Means in the form of a conventional variable flow IV clamp 38 is carried by tube 36 external of radio frequency device 16 for regulating the flow of electrolytic solution through tube 36.

Tube 24 is provided with an additional passageway extending between its proximal and distal extremities 24a and 24b for removing the electrolytic solution from skin 17. A second tubular member or inner tube 41 is disposed within tube 24 in this regard. Inner tube 41 is made from any suitable material such as ABS, nylon, polyethylene or polyester. As illustrated in FIGS. 2–4, inner tube 41 has proximal and distal extremities 41a and 41b and is provided with a passageway in the form of second passageway 42 extending longitudinally therethrough. The material of inner tube 41 can be clear to permit viewing of the fluid traveling therethrough. Inner tube 41 extends along the top of tube 24 and is secured to cylindrical inner surface 29 by any suitable means such as epoxy 43 (see FIG. 3). Inner tube 41 has a generally planar end surface 46 disposed proximal of tube orifice 28 for facilitating the removal of the electrolytic solution from the skin of the patient. It can be seen from FIG. 4 that end surface 46 is disposed at the distal end or tube proximal portion 31 adjacent pliable distal end 32. Second passageway 42 is diametrically sized so as to permit a return flow of electrolytic solution which can approximate the supply flow of the electrolytic solution through first passageway 27 of tube 24.

A return tube 47 extends through handle 23 to proximal extremity 41a of inner tube 41. Return tube 47 has a passageway 48, shown in FIG. 7, extending longitudinally therethrough which communicates with second passageway 42. The return tube 47 extends from handle 23 to a conventional pressure sealed container 49 which is coupled to a conventional suction source (not shown) by tube 51 so as to provide a negative pressure within second passageway 42 for removing the electrolytic solution from the skin of the patient.

Finger operable means is carried by handle 23 for regulating or adjusting the flow rate of the electrolytic solution through tube passageway 48 and thus the amount of the electrolytic solution accumulating on skin 17 at orifice 28. In this regard, handle 23 includes a generally planar top wall 56 having an elongate slot 57 therein which is generally rectangular in shape (see FIGS. 6 and 7). A cylindrical member in the form of wheel 58 is disposed within slot 57. Suction control wheel 58 is formed with first and second rollers 61 which are aligned on the longitudinal centerline of wheel 58 and rotatably engage the underside of top wall 56 on either side of slot 57. Return tube 47 extends below the top wall 56 and rests upon a generally planar surface 62 which faces the underside of top wall 56 and is inclined at a slight angle to the top wall. Support surface 62 is spaced from top wall 56 and suction control wheel 58 is diametrically sized so that as the wheel 58 rolls within slot 57 toward tube 24, the wheel 58 presses further downwardly into the flexible return tube 47. Thus, the cross-sectional area of passageway 48, and the rate of flow through passageway 48, is reduced in proportion to the travel of suction control wheel 58 upwardly through slot 57. Disposition of wheel 58 at the bottom of slot 57 results in an unobstructed passageway 48 and thus full flow through return tube 47. Conversely, positioning of wheel 58 at the top of slot 57 near tube 24 results in closure of return tube passageway 48. A portion of the outer cylindrical surface of suction control wheel 58 extends above top wall 56 to facilitate rolling of the wheel upwardly and downwardly within slot 57 by a thumb of the operator. As illustrated in FIG. 6, gradations are provided alongside slot 57 on the outside of top wall 56. Accordingly, the rate of flow through return tube 47 can be determined by the position of wheel 58 on handle 23.

An electrode 66 is carried by distal extremity 24 of tube 24 for providing electrical energy to the electrolytic solution being supplied to skin 17 through first passageway 27. Electrode 66 is made from any suitable conductive metal such as stainless steel, platinum, gold or silver and, as shown in FIGS. 2, 4 and 5, is ring-like or circular in conformation. More specifically, electrode 66 is oval in conformation. At least one opening in the form of hole 67 extends through the center of ring electrode 66 for permitting the electrolytic solution to flow through the electrode 66. Electrode 66 is disposed within first passageway 27 proximal of orifice 28 by any suitable means such as an adhesive (not shown) and, as shown in FIGS. 2 and 4, is secured to cylindrical inner surface 29 at the end of tube proximal portion 31. The electrode 66 is aligned parallel with end surface 33 and is spaced from the end surface 33 and orifice 28 by a distance equal to the length of distal end 32.

Means for supplying radio frequency energy to electrode 66 includes radio frequency generator and controller 68. Lead means in the form of electrical wire 47 serves to connect generator 68 to electrode 66. The wire 71 extends through handle 23 and first passageway 27 and has a distal end electrically coupled to electrode 66. The proximal end of wire 71 is carried by a cable 72 which connects RF generator and controller 68 to handle 23. A conventional on/off switch 73 is coupled to the wire 71 in handle 23 and is included within the finger operable means of device 16 for controlling the supply of radio frequency energy to electrode 66. Alternatively, said finger operable means can be of a type to vary the power from generator 68 to electrode 66 and be within the scope of the present invention.

Temperature sensing means in the form of thermocouple 76 is carried by distal extremity 24b of tube 24 for monitoring the temperature of the electrolytic solution at orifice 28 (see FIG. 6). Thermocouple 76 is mounted to inner surface 29 of tube proximal portion 31 in the vicinity of electrode 66 by any suitable means such as an adhesive (not shown) and extends proximally through tube 24 to handle 23. The thermocouple wire 76 extends through cable 72 to controller 68. Controller 68 and electrode 66 also permit the impedance of skin 17 and the tissue within the body of the patient to be monitored.

In operation and use, radio frequency device 16 serves to introduce monopolar radio frequency energy through the skin of a patient to tighten the outer surface of the skin. Radio frequency device 16 is particularly suited for treating wrinkles 18 for cosmetic purposes by tightening the skin 17 forming the wrinkle and thus reducing the wrinkle.

The patient to be treated is prepared by placing an indifferent electrode (not shown) on the backside of the patient and electrically coupling the indifferent electrode to radio frequency generator and controller 68. Radio frequency device 16 is prepared by coupling supply tube 36 to the supply container 37 having the electrolytic solution therein. Variable IV clamp 38 is closed to preclude the solution from flowing through tubes 36 and 24. Return tube 47 is connected to suction container 49 which, in turn, is connected to the suction source by means of tube 51. Suction control wheel 58 is positioned at the top of slot 57 so as to crimp and close off return tube 47.

The power requirements of radio frequency device 16 are a function of several factors, including the amount of power applied to electrode 66, the size of electrode 66, the area of orifice 28, the temperature of the electrolytic solution supplied through first passageway 27 and the rate of flow of the electrolytic solution through the first passageway. In this regard, radio frequency energy is delivered by electrode 66 at power levels which can range from 10 to 50 watts with the surface area of the electrode 66 ranging from 0.3 to 1.5 square inches. The electrolytic solution supplied through first passageway 27 has a temperature ranging from 10° to 37° C. and preferably approximately 20° C. The flow rate of the electrolytic solution through first passageway 27 ranges from 50 to 400 drops per minute and more preferably ranges from 200 to 300 drops per minute.

The operator grasps radio frequency device 16 by handle 23 to position distal end 32 against skin 17 so that end surface 33 engages the skin and orifice 28 extends over wrinkle 18 as shown in FIG. 1. The flow of the electrolytic solution is commenced through first passageway 27 by adjustment of IV clamp 38 and suction control wheel 58 is rolled downwardly through slot 57 to desirably adjust the return flow of the electrolytic solution. The relative flow rates between first passageway 27 and second passageway 42 can thus be adjusted to permit the electrolytic solution to puddle in orifice 28 atop wrinkle 18 before the liquid is removed from skin 17 by means of inner tube 41. In this regard, once the maximum desired flow through tubes 36 and 24 has been provided by adjustment of clamp 38, the operator can adjust the amount of electrolytic solution accumulating at tube distal extremity 24b by merely adjusting the outflow of the solution through tubes 41 and 47. The clear material of tube 24 permits the operator to visualize and monitor the electrolytic solution accumulating inside distal extremity 24b to facilitate the adjustment of the flow rates in passageways 27 and 42 The flexible and conformable material of distal end 32 inhibits electrolytic solution from seeping out onto skin 17 around orifice 28.

Once the desired flow of electrolytic solution into first passageway 27 and out of second passageway 42 has been obtained so as to cause the electrolytic solution to accumulate in tube 24 to the level of electrode 66, the operator of radio frequency device 16 pushes button 73 to commence the supply of radio frequency energy to electrode 66. The radio frequency energy from electrode 66 is carried by the electrolytic solution to the outer surface of skin 17. Electrode 66 is in close proximity to orifice 28 and skin 17 so as to minimize energy losses between the electrode and the skin. The radio frequency energy from the electrolytic solution travels through the skin into the body of the patient to the indifferent electrode. The return of the radio frequency energy from the indifferent electrode to generator and controller 68 completes the electrical circuit. The radio frequency energy causes oscillation of the ions in the intercellular solutions of the skin so as to create thermal energy.

The concentration of radio frequency energy is greatest at the skin 17 underlying orifice 28 and is reduced exponentially as a function of the distance from the radio frequency source, that is the distance beneath skin 17 from orifice 28. Specifically, the temperature effects from radio frequency energy are determined by the following equation:

$$\text{Temperature rise} = (k)(I^2)(t)/(r^4)$$

where "k" is a constant for a given power impedance condition, "I" equals current, "t" equals time and "r" is the radius or distance from the radio frequency source, that is the electrolytic solution at the outer surface of skin 17. In FIG. 8, the temperature of the skin 17 produced by radio frequency-induced molecular friction as a function of the distance beneath skin 17 is depicted by the dashed line 81. As can be seen, the radio frequency-induced temperature is greatest in the outer layer or epidermis of skin 17 adjacent orifice 28.

The electrolytic solution additionally serves to cool skin 17 at orifice 28 thus counteracting the effects of molecular friction caused by the radio frequency energy passing through the skin surface. The actual temperature of skin 17 as a function of the distance below the surface of the skin is shown by the solid line 82 in FIG. 8. As can be seen in FIG. 8, the effects of cooling by the electrolytic solution diminish at levels below the skin surface. Thus, the temperature in these lower skin levels is high relative to the temperature of the outer layers of the skin. In this manner, the thermal heating of the dermis layer of the skin 17 is achieved with reduced heating of the epidermis layer of the skin 17.

The transmission of radio frequency energy through the skin 17 results in a secondary temperature rise at skin depths where the temperature effects from molecular friction are rapidly decreasing. This temperature rise is caused by conductive heating generated from radio frequency-induced molecular friction. It can be seen from FIG. 8, for example, that the actual temperature 82 of the skin 17 crosses over the radio frequency temperature 81 at approximately 1.8 millimeters below the surface of the skin so that the actual skin temperature 82 is approximately 5° to 10° higher than the radio frequency-induced temperature of skin 17 at distances greater than approximately 1.8 millimeters below the surface of the skin.

The optimal heating profile or gradient of skin 17 is set forth in FIG. 8. As shown therein, a more uniform temperature distribution is obtained across the wall of the skin than would be achieved by merely heating the surface of the skin. Specifically, the skin temperature two millimeters below the surface ranges from 62° to 70° C. and preferably approximately 65° C. This dermis temperature is maintained for a period ranging from one to four seconds. The skin temperature decreases exponentially in the deeper layers of the skin. The desired temperature in the epidermis layer of skin 17 is 60° C. or less, preferably ranging from 37° to 60° C. and more preferably approximately 55° C. The temperature of skin 17 is monitored by means of thermocouple 76 at controller 68, which can calculate the skin temperature from the temperature of the electrolytic solution at thermocouple 76. The impedance of skin 17 is also monitored at the controller 68. The procedure at a particular site on skin 17 can be terminated, either manually or automatically, if the skin temperature or impedance reach certain levels.

The flow of radio frequency energy through skin 17 denatures the collagen molecules within the skin and thus serves to tighten the outer layer or epidermis of the skin being treated. In this regard, the radio frequency induced thermal energy breaks apart the heat sensitive bonds between the fibrils of the trifibrillar helix in the collagen molecules. When these bonds are broken, each of the fibrils shrinks to a shortened or contracted state. Once the thermal heating is reduced, the fibrils cross-link in a random coil as opposed to the organized fibril network which existed prior to heating. This contraction of the collagen stroma serves to similarly contract the outer layer of skin 17.

Radio frequency device 16 serves to enhance collagen shrinkage in skin 17 by increasing the flow of radio frequency energy to the dermis layer of the skin. Since greater amounts of collagen exist in the dermis layer than in the epidermis layer of skin, it is desirable that the radio frequency induced thermal energy be concentrated in the dermis layer rather than in the epidermis layer. The radio frequency energy from device 16 creates a slow heating of skin 17 so as to permit temperatures in the dermis layer to rise without necrosis and charring to the epidermis. Such charring causes undesirable impedance rises in the epidermis layer of the skin 17 which decreases the electrical transmissivity of the epidermis layer and thus the flow of electrical energy to the underlying dermis layer. The thermal heating of the epidermis is decreased, as illustrated in FIG. 8, by the continuous cooling of the epidermis from the flow of electrolytic solution traveling through tube 24.

The method of the present invention is less painful to the patient than existing procedures. The cooling of the outer layer of skin 17 minimizes painful burns which would otherwise result in these layers. The spacing of electrode 66 from skin 17 also reduces the likelihood of skin burns by inhibiting intimate contact between the thermally hot electrode and the skin. The deep penetration of the radio frequency energy reduces pain to the patient by deadening nearby nerve endings in the skin. In addition, the level of sloughing of the outer layers of skin 17 is decreased.

The operator of radio frequency device 16 moves distal end 32 along the wrinkle 18 or the other portion of the skin 17 being treated. This movement can be in sequential steps or in a continuous motion. The flow of electrolytic solution and radio frequency energy through tube 24 is continuous during such movement and the conformable material of tube distal end 32 acts as a squeegee to remove the electrolytic solution from skin over which it passes. In this manner, the desired portion of skin 17 is treated.

Upon completion of the procedure, button 73 is depressed to cease the flow of electrical energy from radio frequency generator and controller 68. IV clamp 38 is closed off to cease the flow of the electrolytic solution to radio frequency device 16 and supply tube 36 is disconnected from supply container 37. Suction control wheel 58 is rolled upwardly in slot 57 once any remaining electrolytic solution on the skin of the patient has been removed through return tube 47.

It should be appreciated that orifice 28 can be rectangular in shape or have other shapes. The radio frequency device of the present invention can also have interchangeable tubes 24 and/or distal ends 32 for accommodating different contours in the surface of skin 17. Leakage of the electrolytic solution can thus be further minimized. Electrolytic solutions with higher viscosity will also be less susceptible to leaking from distal end 32 of the device 16. More consistent applications are provided with larger orifices 28. However, such larger orifices require more radio frequency power.

From the foregoing it can be seen that a new and improved radio frequency device and method for resurfacing skin has been provided which minimizes burning of the superficial layers of the skin. Collagen molecules in the skin are denatured to tighten the epidermis layer of the skin and thus resurface the skin. Radio frequency energy is carried by an electrically conductive liquid to the surface of the skin. A flow of the electrically conductive liquid engages the skin to actively cool the skin.

What is claimed is:

1. A radio frequency device for use on a human to treat a wrinkle in skin having collagen therein comprising a handle member having an end portion adapted to engage the skin, the end portion being provided with an opening and an internal cavity communicating with the opening, a flexible conformable surface circumscribing the opening for engaging the skin so that the opening overlies at least a portion of the wrinkle, the handle member having a first passageway extending through the handle member to the cavity in the end portion, a reservoir coupled to the handle member for supplying an electrically conductive liquid through the first passageway to the cavity to contact the portion of the wrinkle circumscribed by the opening, an electrode carried by the end portion proximal of the opening so as not to contact the skin, the electrode being in electrical communication with the first passageway for providing electrical energy to the conductive liquid, a radio frequency generator for supplying radio frequency energy to the electrode, a return path in electrical contact with the human remote from the handle member and electrically coupled to the radio frequency generator, the handle member having a second passageway extending to the cavity in the end portion for removing the conductive liquid from the cavity whereby the radio frequency energy in the conductive liquid contacting the skin causes resistive heating in the skin so as to contract the collagen and thus treat the wrinkle, the engagement of the surface with the skin inhibiting the conductive liquid from leaking outside of the opening and thus protecting skin not being treated.

2. A device as in claim 1 further comprising finger operable means carried by the handle for regulating the rate of flow of the conductive liquid through the second passageway.

3. A device as in claim 1 wherein the end portion is an elongate tubular member, the first passageway extending through the elongate tubular member.

4. A device as in claim 1 wherein the handle member includes a handle having a shape for grasping by the human hand.

5. A device as in claim 1 wherein the electrode is provided with at least one hole extending therethrough for permitting the conductive liquid to flow through the electrode.

6. A device as in claim 5 wherein the electrode is ring-like in conformation.

7. A device as in claim 5 wherein the end portion is cylindrical and has an inner surface for forming the first passageway, the electrode secured to the inner surface of the end portion.

8. A radio frequency device for use on a human to resurface skin having collagen therein comprising a handle member having an end portion, the end portion having a rubber distal portion adapted to engage the skin, the distal portion being provided with an opening and the end portion having an inner surface forming at least one passageway extending to the opening, a reservoir coupled to the handle member for supplying an electrically conductive liquid through the passageway to the opening, an electrode secured to the inner surface of the end portion proximal of the opening for providing electrical energy to the conductive liquid, a radio frequency generator for supplying radio frequency energy to the electrode and a return path in electrical contact with the human and coupled to the radio frequency generator whereby the radio frequency energy in the conductive liquid contacting the skin at the opening causes the collagen in the skin to contract and thus tighten the skin.

9. A device as in claim 8 wherein the handle member is provided with an additional passageway extending to the end portion for removing the conductive liquid from the end portion.

10. A radio frequency device for use on a patient to treat a wrinkle in skin having a surface and collagen therein comprising a handle member adapted for use by a human hand, the handle member having a flexible, conformable end portion adapted to engage the skin and being provided with an opening and an internal cavity communicating with the opening, the handle member having an inlet passageway extending to the cavity for supplying an electrically conductive liquid to the opening for contacting the wrinkle and having an outlet passageway extending to the cavity for removing the conductive liquid from the cavity, an electrode carried by the end portion proximal of the opening in communication with the cavity for providing radio frequency energy to the conductive liquid, a radio frequency generator coupled to the handle member for supplying radio frequency energy to the electrode, a return path in electrical contact with the patient and electrically coupled to the radio frequency generator whereby the radio frequency energy in the conductive liquid contacting the skin causes resistive heating in the skin so as to contract the collagen in the skin and thus treat the wrinkle, means coupled to the handle member for supplying a cooled conductive liquid to the first passageway for cooling the skin and thus reducing the resistive heating at the surface of the skin so as inhibit burning of the surface of the skin.

11. A device as in claim 10 wherein the electrode is a ring-like electrode disposed in the inlet passageway.

12. A device as in claim 10 further comprising finger operable means carried by the handle member for controlling the supply of radio frequency energy to the electrode.

13. A device as in claim 10 further comprising finger operable means carried by the handle member for adjusting the flow rate of the conductive liquid through the outlet passageway.

\* \* \* \* \*